(12) United States Patent
Saied et al.

(10) Patent No.: US 6,312,412 B1
(45) Date of Patent: Nov. 6, 2001

(54) APPARATUS AND METHOD FOR PAINLESS INTRAMUSCULAR OR SUBCUTANEOUS INJECTIONS

(75) Inventors: V. C. Saied, 2802 Hamilton, Wichita Falls, TX (US) 76308; Patrick A. Dillon, Dallas, TX (US)

(73) Assignee: V. C. Saied, M.D., Wichita Falls, TX (US)

( * ) Notice: Subject to any disclaimer, the term of this patent is extended or adjusted under 35 U.S.C. 154(b) by 0 days.

(21) Appl. No.: 09/204,988

(22) Filed: Dec. 2, 1998

(51) Int. Cl.[7] .................................................. A61M 5/00
(52) U.S. Cl. ............................................................ 604/191
(58) Field of Search ...................... 604/93, 181, 191–198, 604/48, 518, 131, 95.01, 117, 156

(56) References Cited

U.S. PATENT DOCUMENTS

| | | | |
|---|---|---|---|
| 2,696,212 | 12/1954 | Dunmire | 128/216 |
| 2,727,514 | 12/1955 | Lockhart | 128/218 |
| 2,828,742 | 4/1958 | Ashkenaz | 128/218 |
| 3,279,743 | 10/1966 | de la Garza | 251/43 |
| 3,380,450 | 4/1968 | Adelberger | 128/218 |
| 3,512,524 | 5/1970 | Drewe | 128/216 |
| 3,552,394 | * 1/1971 | Horn | 128/218 |
| 3,556,099 | * 1/1971 | Knight . | |
| 3,783,876 | 1/1974 | Dye | 128/347 |
| 3,967,621 | 7/1976 | Schwarz | 128/216 |
| 3,995,629 | 12/1976 | Patel | 128/215 |
| 4,150,669 | * 4/1979 | Latorre | 128/79 |
| 4,226,235 | * 10/1980 | Sarnoff et al. . | |
| 4,613,328 | * 9/1986 | Boyd . | |
| 4,664,656 | 5/1987 | Taddei | 604/241 |
| 4,740,205 | 4/1988 | Seltzer et al. | 604/192 |
| 4,758,230 | 7/1988 | Rycroft | 604/118 |
| 4,799,926 | 1/1989 | Haber | 604/187 |
| 5,190,521 | 3/1993 | Hubbard et al. | 604/51 |
| 5,423,752 | * 6/1995 | Haber et al. | 604/86 |
| 5,505,694 | 4/1996 | Hubbard et al. | 604/51 |
| 5,971,953 | * 10/1999 | Bachynsky | 604/90 |

FOREIGN PATENT DOCUMENTS

| | | |
|---|---|---|
| 292032 | 6/1928 | (GB) . |
| 1191634 | 5/1970 | (GB) . |

* cited by examiner

Primary Examiner—Sharon Kennedy
Assistant Examiner—Catherine Serke
(74) Attorney, Agent, or Firm—Munsch Hardt Kopf & Harr, P.C.

(57) ABSTRACT

A painless injection apparatus includes a first injector having a first storage chamber storing a numbing agent, a first needle, and a first plunger, and a second injector having a second storage chamber storing a medication, a second needle, and a second plunger. The injection apparatus further includes a plunger actuation device coupled to the first and second plungers and the second storage chamber. The plunger actuation device is adapted to sequentially advance the first plunger, the second storage chamber, and then the second plunger to inject the numbing agent and then the medication painlessly into a patient's tissues at the desired depths. The needles and medicine storage chambers are enclosed in a disposable portion of the injection apparatus which can be disposed of properly.

36 Claims, 14 Drawing Sheets

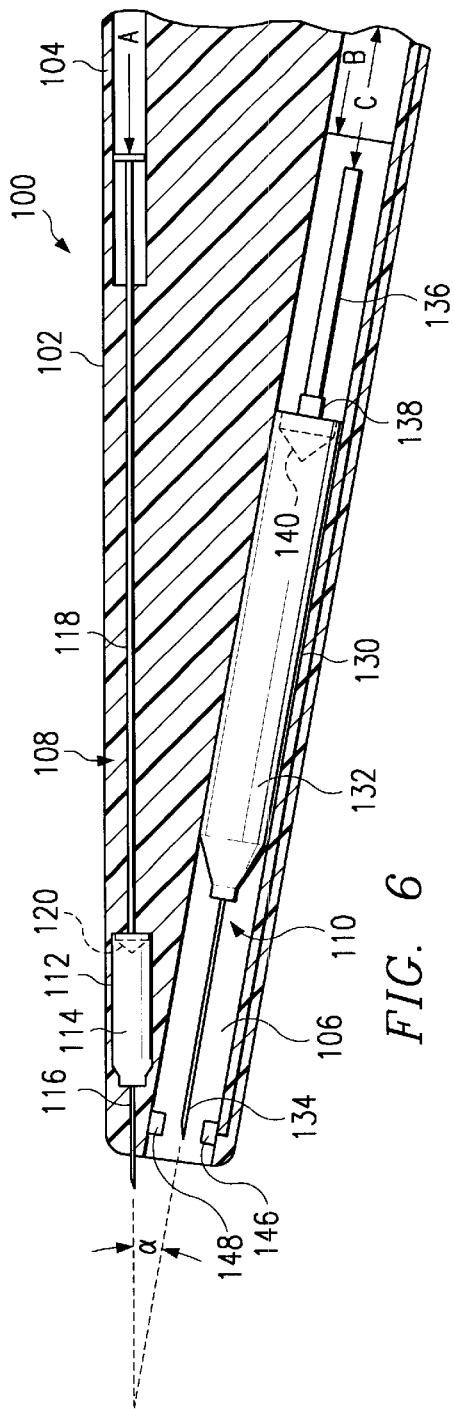
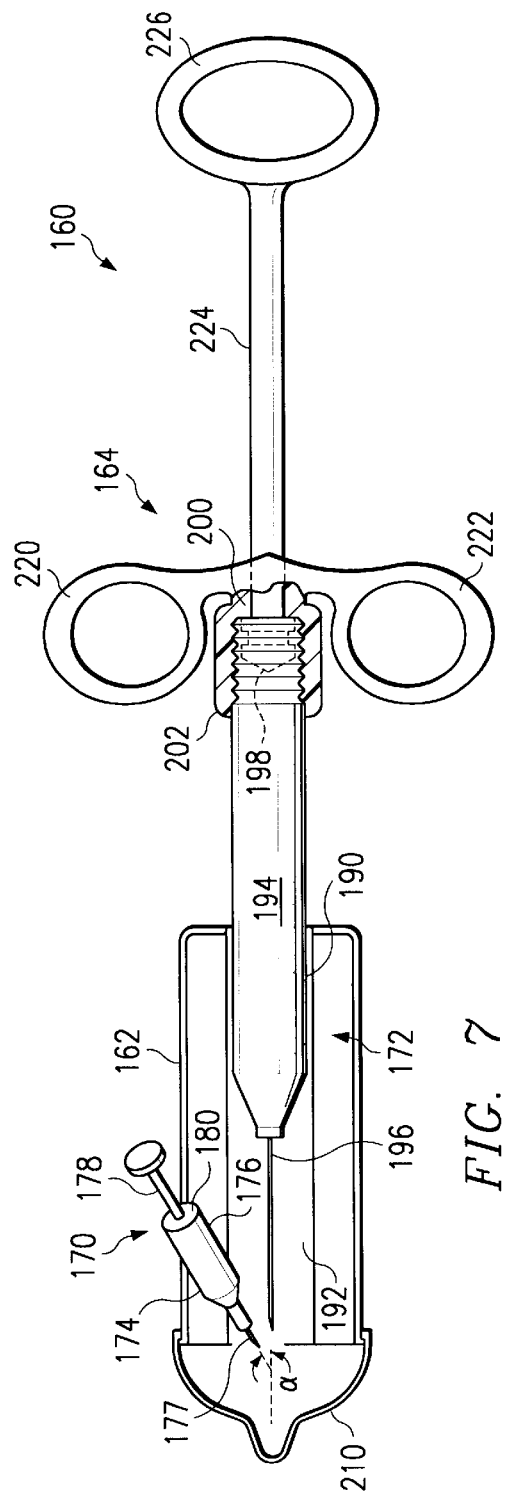
FIG. 6
FIG. 7

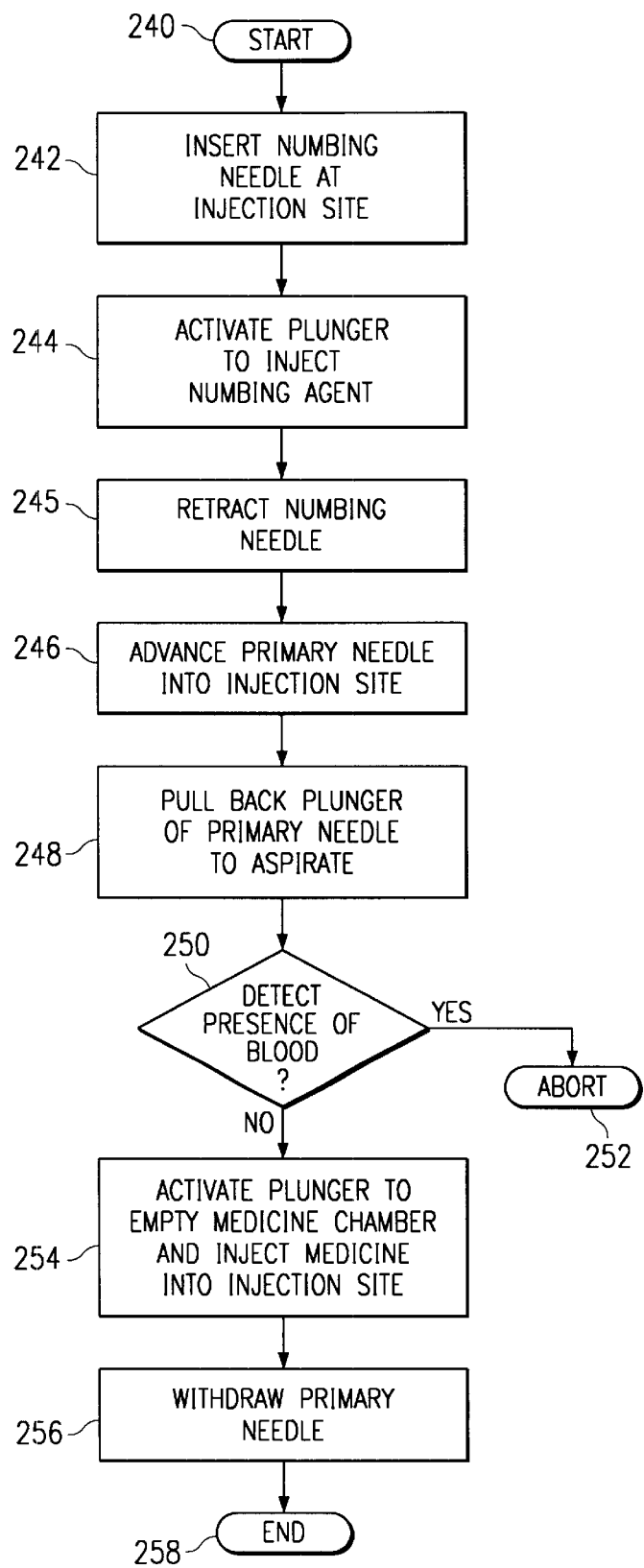

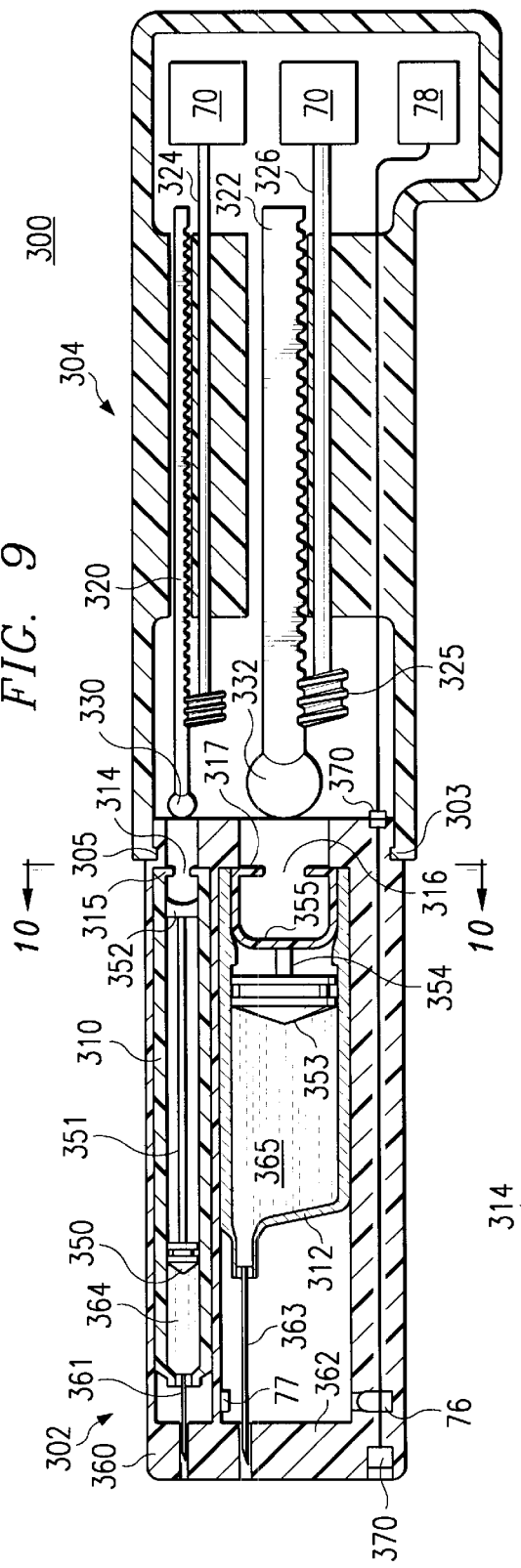

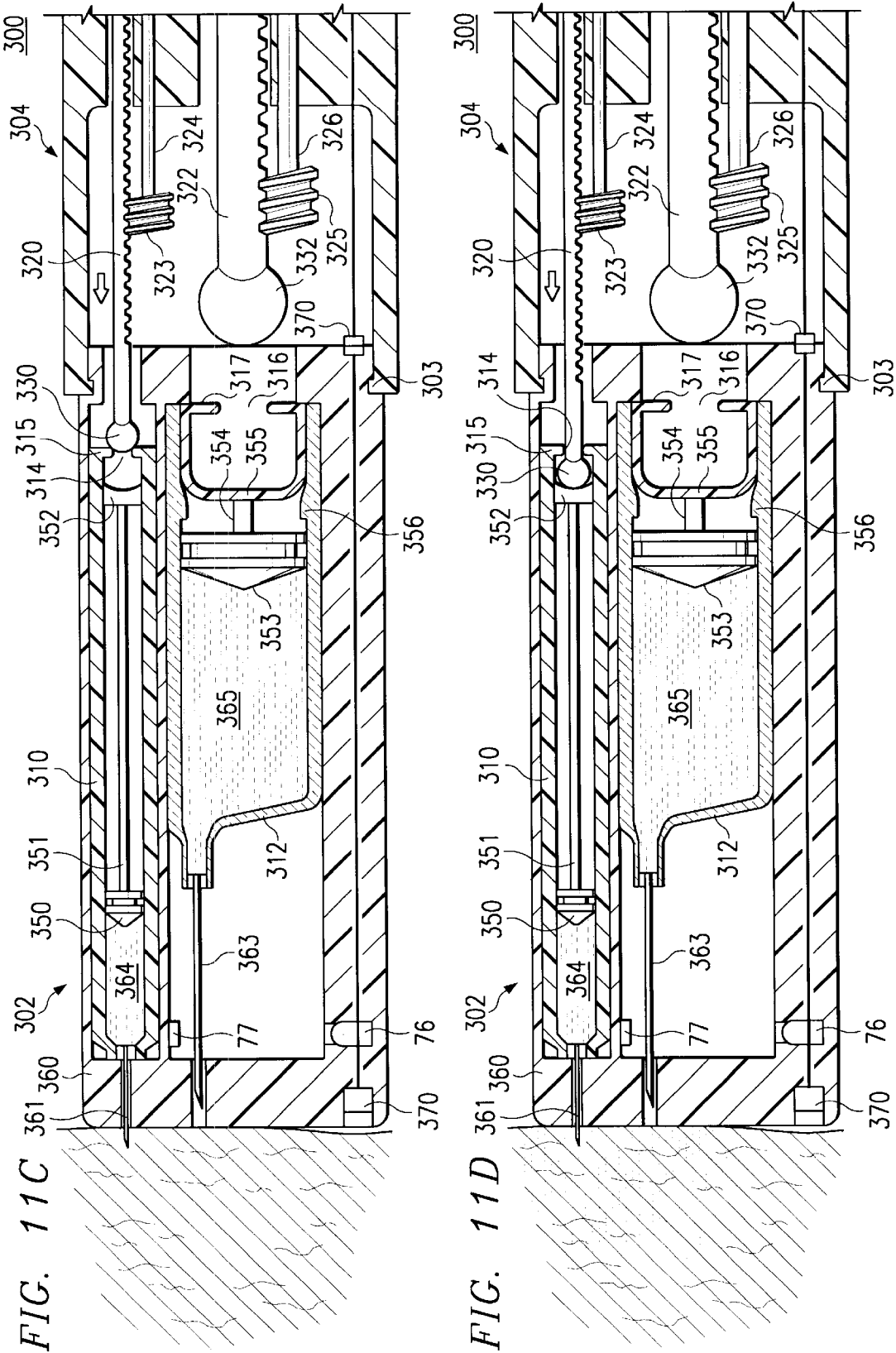

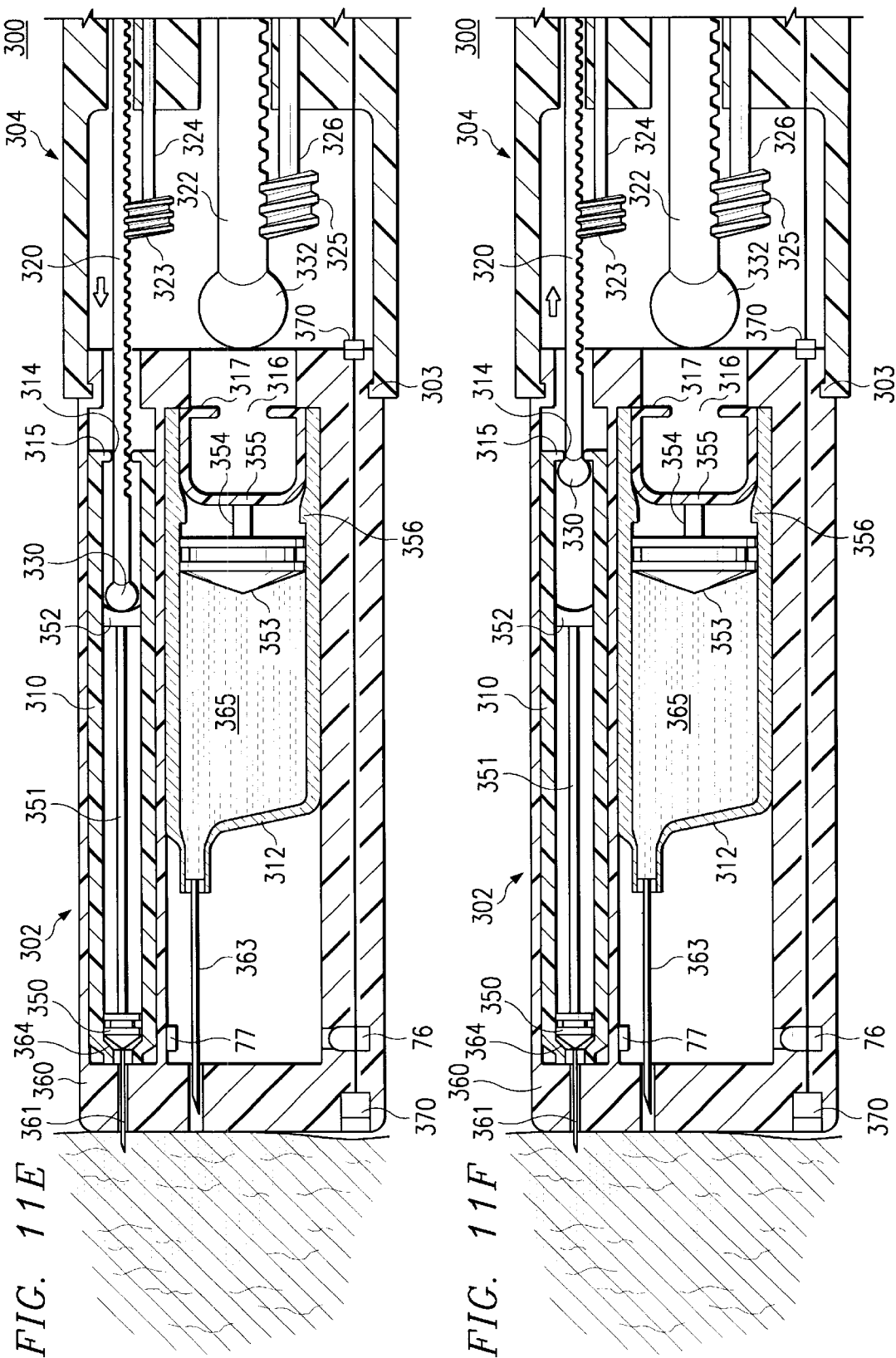

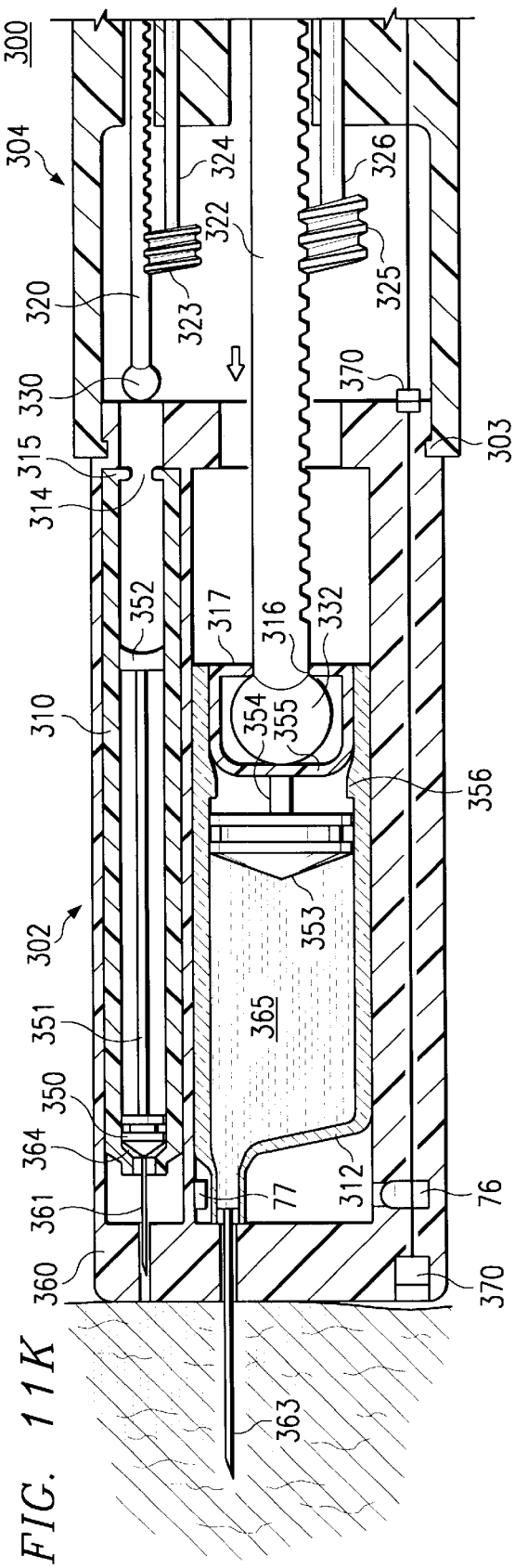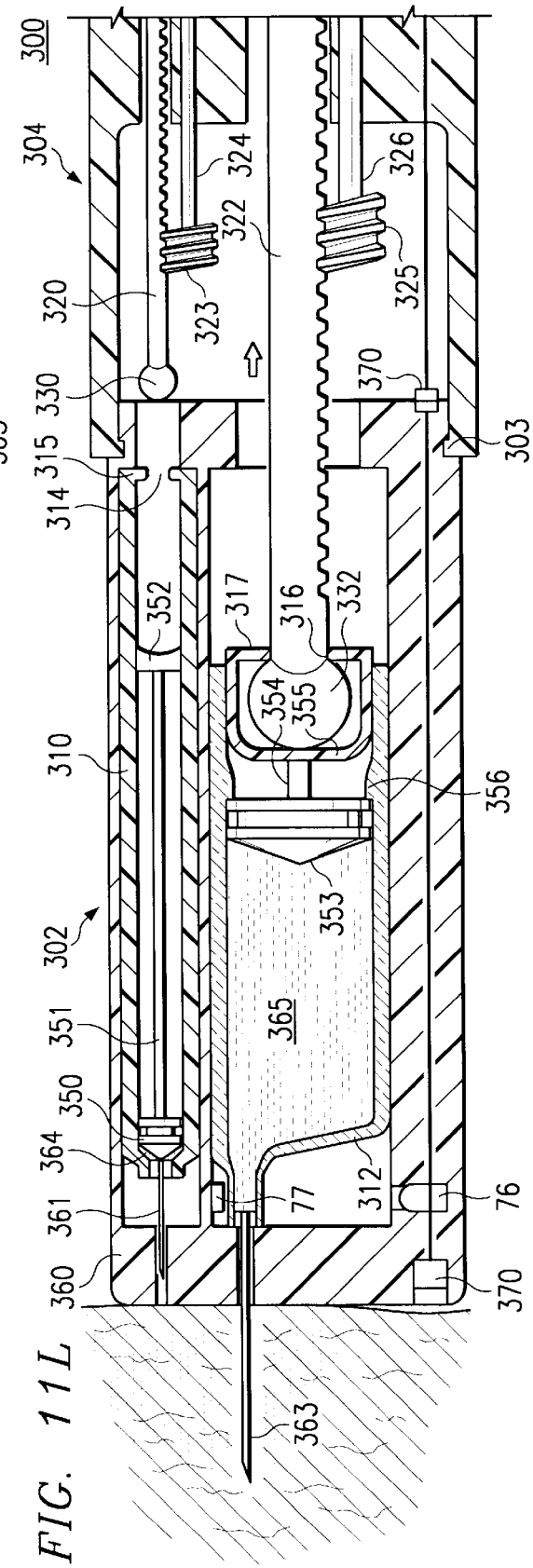

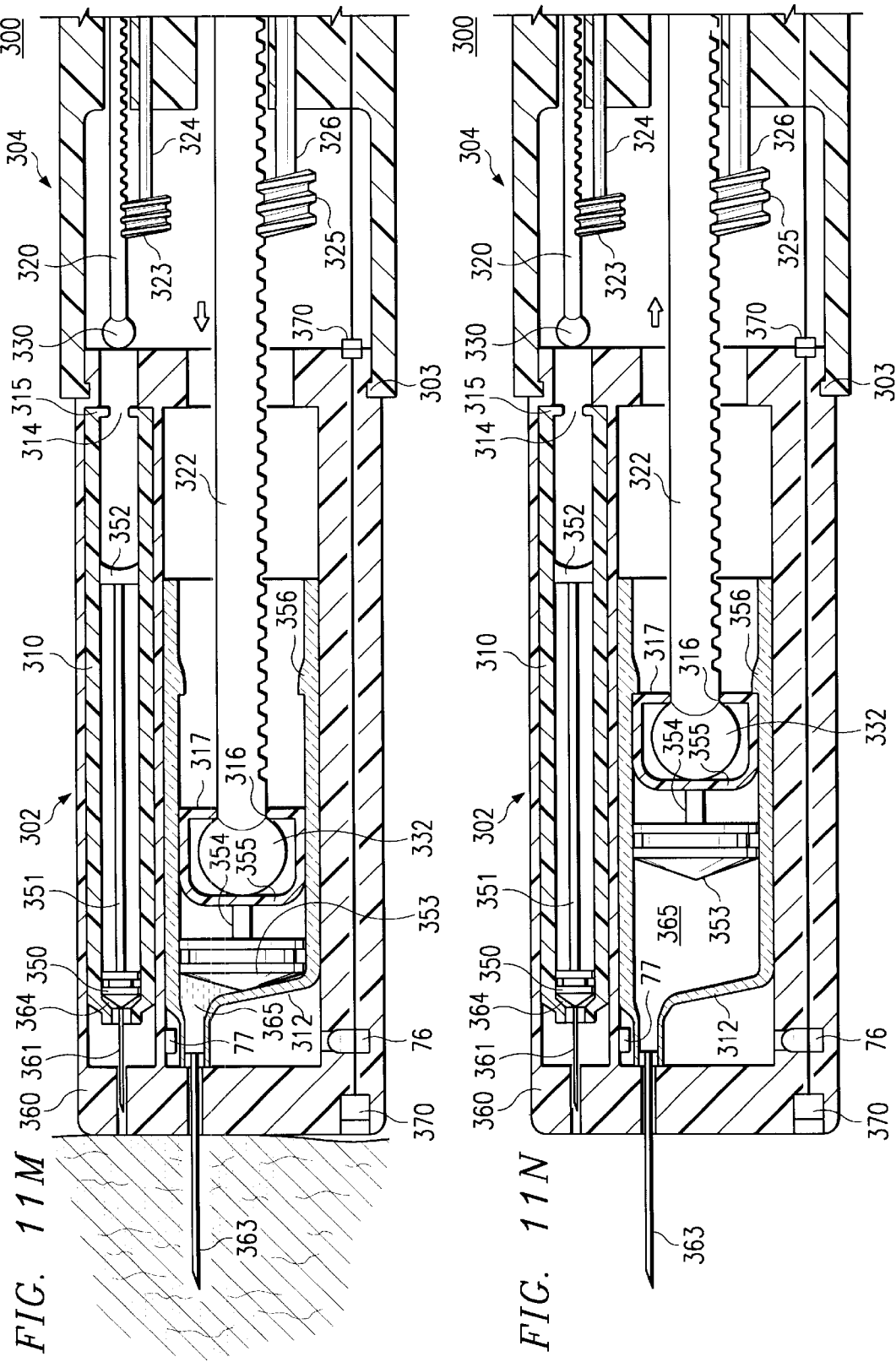

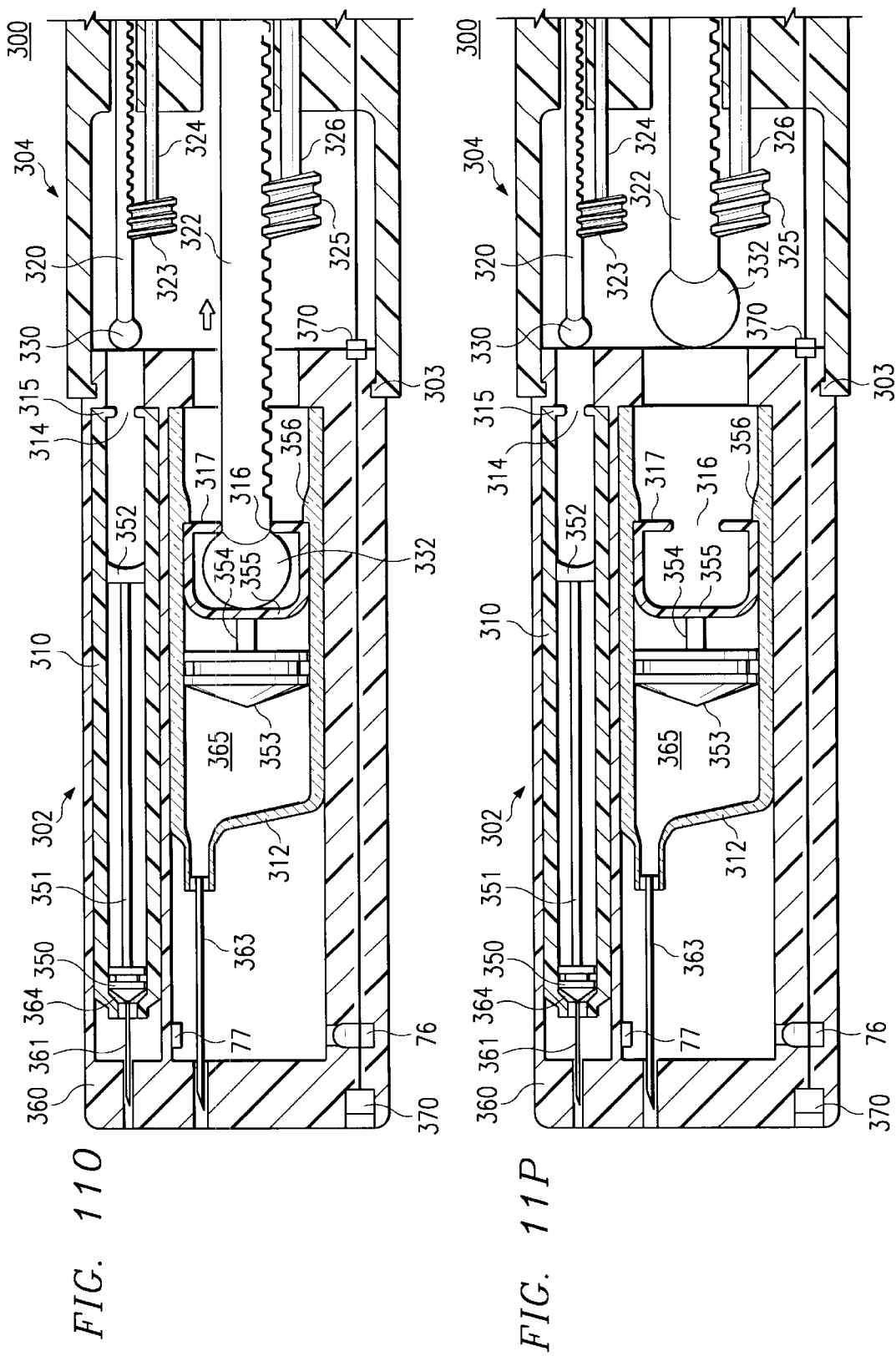

APPARATUS AND METHOD FOR PAINLESS INTRAMUSCULAR OR SUBCUTANEOUS INJECTIONS

TECHNICAL FIELD OF THE INVENTION

This invention relates in general to medical products, and more particularly to apparatus and method for painless intramuscular or subcutaneous injections and safe disposal thereof.

BACKGROUND OF THE INVENTION

Most people dread needles. The sight alone of a large needle is enough to cause many patients to become anxious and tense. This reaction in turn may cause the patient's muscles to become tight and hard, making needle penetration even more difficult and painful.

Many medications must be injected intramuscularly with a substantially large needle necessary to penetrate the muscle layers and transfer more viscous medications through the needle. These types of injections are painful, because the long needle penetrates deeply through the layers of skin as well as many layers of muscles.

Intramuscular injections involve injecting a medication into the muscle layers. To avoid injecting the medication intravascularly, an extra step is taken by aspirating the syringe after the needle is inserted but prior to depressing the plunger. If blood is drawn up into the syringe, then the tip of the needle has entered a blood vessel, and the needle must be repositioned in order to clear the vessel. Some health care workers may forget or skip this step, which may cause adverse effects when the medication is injected intravascularly.

Accordingly, it has become desirable to provide an injection device that first injects a numbing agent at the site of injection with a fine gauge needle, and then inserts the larger medication needle through the anesthetized skin painlessly and then injects the medication intramuscularly at the desired depth. The numbing of the skin is almost immediate.

In one aspect of the invention, a painless injection apparatus includes a first injector having a first storage chamber storing a numbing agent, a first needle, and a first plunger, and a second injector having a second storage chamber storing a medication, a second needle, and a second plunger. The injection apparatus further includes a plunger actuation device coupled to the first and second plungers and the second storage chamber. The plunger actuation device is adapted to sequentially advance the first plunger, the second storage chamber, and then the second plunger to inject the numbing agent and then the medication painlessly through the skin.

In another aspect of the invention, a method for painless injections includes the steps of inserting a first fine gauge needle of a first injector into a patient's skin, and actuating a first plunger of the first injector to inject a numbing agent into the patient's skin. Thereafter, a second plunger is actuated to advance and insert a second needle of a second injector positioned in close proximity to the first injector and forming an integral unit therewith through the patient's anesthetized skin to a desired depth. A third plunger of the second injector is then actuated to retract the medication plunger a predetermined amount to aspirate for blood. If blood is not detected, the third plunger of the second injector is actuated to inject a medication to the desired depth in the patient's tissues.

Another aspect of the device is that it could be adjusted to insert the medication needle to varying depths to allow for varying thicknesses of muscle and/or subcutaneous tissue or fat.

A technical advantage of the invention includes the availability of an essentially painless intramuscular or subcutaneous injection with the convenience of one integrated injection device. Additionally, with the use of pre-filled and pre-labeled medication cartridges, the incidence of dosage errors is greatly reduced, and wrong medication accidents would be less likely. With automatic aspiration, the occurrence of injecting a medication intravascularly when an intramuscular injection is intended is eliminated. A further technical advantage includes the lessening of the patient's anxiety and muscle tightening at the sight of a large needle because the device does not look like a "shot" and the medication needle is not visible. Another advantage of the device is that it could be adjusted to insert the medication needle to varying depths to allow for varying thickness of muscle and/or subcutaneous tissue or fat. An additional advantage of the injection device provides for an automatic retraction of the needles into the housing, so that accidental and inadvertent needle stick is essentially eliminated to avoid the transmission of contagious diseases. Further, because there is no exposed needles, safe disposal of used cartridges is also possible.

BRIEF DESCRIPTION OF THE DRAWINGS

For a better understanding of the present invention, reference may be made to the accompanying drawings, in which:

FIG. 6 is a cross-sectional view of another embodiment of the injection device in which the fine gauge needle adapted to inject the numbing agent is positioned at a predetermined acute angle with respect to the larger needle adapted to inject the medication;

FIG. 7 is a cross-sectional view of yet another embodiment of the injection device adapted for manual plunger actuation;

FIG. 8 is a flowchart of an exemplary procedure for making a painless injection using the injection device of the present invention;

FIG. 9 is a cross-sectional view of an exemplary embodiment of a mechanical coupling and actuation mechanism of the injection device according to the teachings of the present invention;

FIG. 10 is a cross-sectional view, taken along line 10—10, of the exemplary embodiment of FIG. 9 according to the teachings of the present invention.

DETAILED DESCRIPTION OF THE INVENTION

Figure 1:
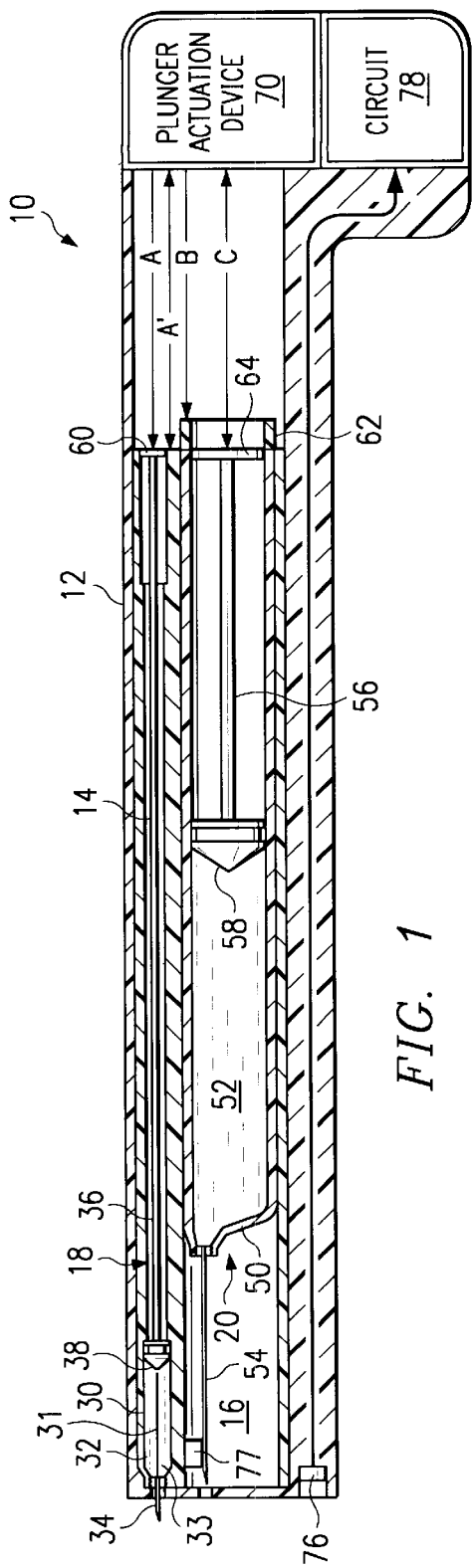
FIG. 1 is a cross-sectional view of an embodiment of an injection device constructed according to the teachings of the present invention.

Referring to FIG. 1, a cross-sectional view of an embodiment of an injection device 10 constructed according to the teachings of the present invention is shown. Injection device 10 includes an injector housing 12 with two inner housing portions or chambers 14 and 16 placed adjacently with one another. A first injector 18 is housed in first housing portion 14 and a second injector 20 positioned in close proximity to first injector 18 is housed in second housing portion 16.

First injector 18 includes a storage chamber or disposable cartridge 30 that accommodates a numbing agent or solution 32, such as bacteriostatic saline solution, lidocaine, or the like. Storage chamber 30 may also be divided into two chamber sections 32 and 33 to accommodate a numbing agent and a sodium bicarbonate solution, respectively, to further lessen the sensation felt by the patient during the injection. When plunger 38 of first injector 18 is pushed, the solutions from both chamber sections 32 and 33 mix just prior to being injected into the patient's skin, thus making the injection even more painless. A fine gauge needle 34, such as 23 to 30 gauge or finer, is adapted to inject the numbing solution into the patient's skin when plunger 38 is actuated toward needle 34. Plunger 38 includes an elongated member 36 which is used to advance plunger 38 into storage chamber 30. The sharp tip of needle 34 may protrude beyond the tip of injector housing 12. The length of the protrusion represents substantially the desired depth of injection for the numbing agent, which is preferably in the upper layers of skin. The depth may also extend to or below the epidermis layer, the dermis layer, or into the tela subcutaneous layer. It is preferable that cartridge 30 is disposable and can be easily installed in injection device 10.

Second injector 2C includes a storage chamber or disposable cartridge 50 that stores a liquid medication or solution 52. A needle 54 is coupled to storage chamber 50 and in fluid connection therewith to receive medication 52 when a plunger 58 is actuated. Plunger 58 includes an elongated plunger member 56 which is used to advance plunger 58 into storage chamber 50 toward needle 54. It may be clearly seen that it is preferable that needle 54 is positioned generally off-center with respect to storage chamber 50 so that it is in very close proximity to needle 34 of first injector 18. As a result, the entry site of needle 54 is almost at the same entry site of numbing needle 34 to take full advantage of the anesthetizing effect of the numbing injection.

Injection device 10 further includes a plunger actuation device, circuit or mechanism 70. Plunger actuation device 70 is coupled to plunger member 36 of plunger 38 of first injector 18, and storage chamber 50 and elongated plunger member 56 of plunger 58 of second injector 20. Mechanical couplings and actuators 60–64 may be needed to couple or convey actuation signals or displacements labeled A, A', B, and C generated by plunger actuation device 70. Actuation movements or signals A, A', B, and C are adapted to advance and retract plungers 38 and 58 and storage chambers 30 and 50. The operations thereof are described in detail below.

A source or light emitting diode (LED) 76 and a detector or photodetector 77 may be arranged substantially opposed to each other near the end of injector housing 12 in housing portion 16. Light emitting diode 76 may be substituted by any other light or energy source, and photodetector 77 may be substituted by any other suitable detector that is adapted to detect the light or energy emitted by source 76. Photodetector 77 generates a suitable detection signal which is conveyed to a control circuit 78.

Figure 2:
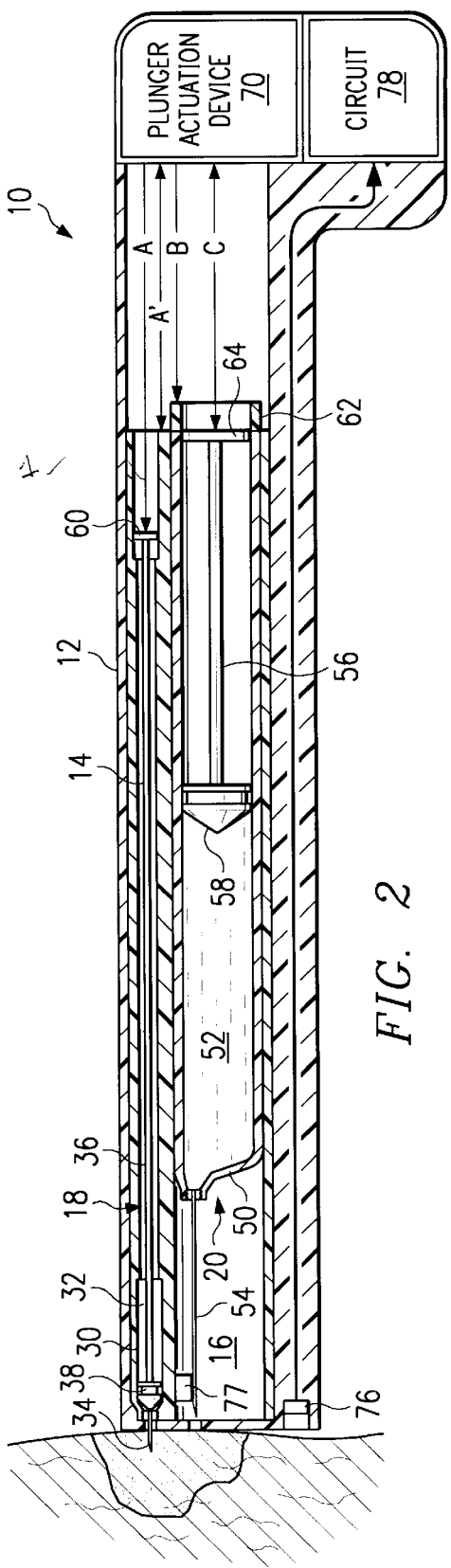
FIG. 2 is a cross-sectional view of the injection device in which a first plunger is actuated to inject a numbing agent through a fine gauge needle into the upper layers of the skin at an injection site.
Figure 3:
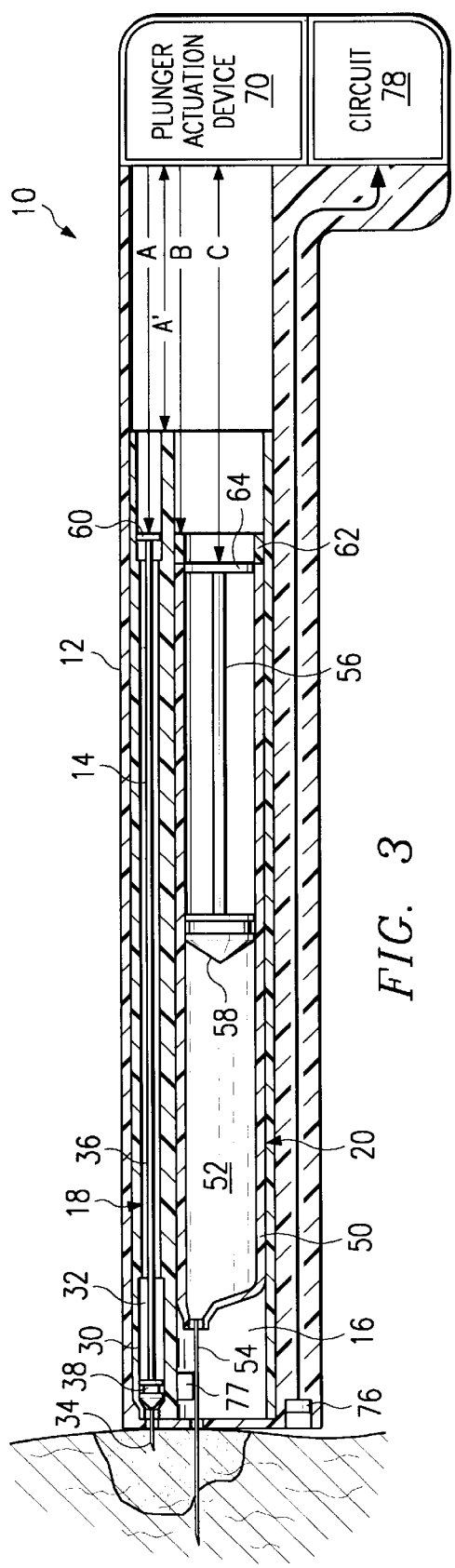
FIG. 3 is a cross-sectional view of the injection device in which a second plunger is actuated to advance a second larger needle to a desired depth at or near the injection site.
Figure 4:
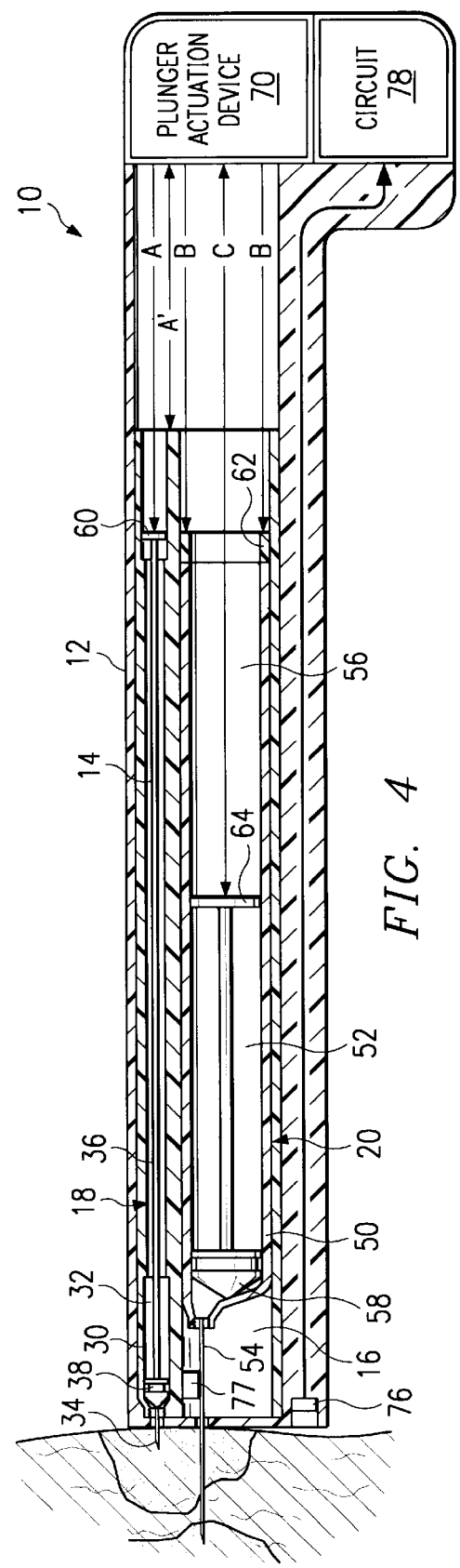
FIG. 4 is a cross-sectional view of the injection device in which a third plunger is actuated to inject a medication to the desired depth.

Referring to FIGS. 2–4, the sequence of plunger actuation according to the teachings of the present invention is shown. The method is also shown in flowchart form in FIG. 8 beginning at block 240. The tip of injection device 10 is first placed against the skin of a patient. Actuating device 70 may then generate displacement or actuation signal A' to advance first injector 18 and insert numbing needle 34 into the skin to the desired depth. Alternatively, fine gauge needle 34 may protrude beyond the tip of injection device 10 as its disposable cartridge 30 is installed therein and may be directly inserted into the patient's skin by the health care professional. Because of the fine gauge of numbing needle 34 and the shallowness of the insertion depth, the patient has very little sensation of the actual needle penetration. Further, because injection device 10 has little or no resemblance to a typical syringe, the heightened stress and sensation accompanying the anticipation of pain is greatly reduced.

In FIG. 2 and also shown in block 244 of FIG. 8, plunger actuation device 70 may then generate displacement or actuation signal A to advance plunger 38 of first injector 18. Plunger 38 causes the numbing agent in storage chamber 30 or the sub-chamber sections 32 and 33 to empty through needle 34 and be injected at the desired depth in the patient's skin. Preferably, a small skin wheal is raised by the injected numbing solution. The numbing needle is then retracted from the patient's skin by actuation signal A' or displacement generated by plunger actuation device 70. This is also shown in block 245 in FIG. 8.

In FIG. 3, plunger actuation device 70 further generates displacement or actuation signal B to advance second injector 20 toward the tip of injection device 10, so that needle 54 now protrudes beyond the tip and through the patient's skin and into subcutaneous and/or muscle tissues. This is also shown in block 246 in FIG. 8.

It may be desirable to allow a short predetermined time lapse, such as two or three seconds, between the numbing agent injection and the insertion of needle 54 to allow the anesthesia ample time to take effect. The amount of needle advancement may be controlled by a switch (not shown) located on housing 12 that may be used to indicate the desired depth of penetration depending on whether an intramuscular or a subcutaneous injection is intended or depending on the thickness of the individual's tissues. The health care professional may set the switch to a first position indicating an intramuscular injection and to a second position indicating a subcutaneous injection, where the amount of advancement for intramuscular injections is greater than that of the subcutaneous injection.

Thereafter, plunger actuation device 70 generates displacement or actuation signal C to retract plunger 58 a predetermined amount to aspirate for blood, as shown in block 248. If the tip of needle 54 has stopped intravascularly, the retraction of plunger 58 causes a small amount of blood to be aspirated into storage chamber 52 sufficient to block or obscure the transmission of light or energy from source 76 to detector 77 or cause the transmission of an unsuitable signal. At the presence of blood, detector 77 generates a detection signal indicative of whether blood was detected in storage chamber 50. If blood is detected, then the procedure is aborted, as shown in blocks 250 and 252.

If blood is not detected, then control circuit 78 informs plunger actuation device 70 and instructs it to generate displacement or actuation signal C to advance plunger 58 to inject medication 52. This is shown in FIG. 4 and block 254 in FIG. 8. In block 256, the injection is completed. Plunger actuation device 70 then retracts second injector 20 and needle 54 back into housing 12 so that no contaminated needle is exposed to accidentally prick health care professionals or any person who may handle the discarded injector. A visual indicator, such as a light emitting diode (not shown) located on injector housing 12 and coupled to plunger actuation device 70 or circuit 78 may be used to inform the health care professional that the injection process is completed. Injection device 10 is then withdrawn from the patient. The procedure ends in block 258. The disposable cartridge is then properly disposed of in a safe manner.

Because needles 34 and 54 are arranged in very close proximity with one another, the anesthetizing effect of numbing agent 52 is fully realized as needle 54 is inserted into the patient's skin and muscle tissues and the medication is injected. At all times, the main injection needle is not visible to the patient, thus lessening the heightened sensitivity and anxiety caused by anticipation and fear. The entire sequence of injection as described above may be automated by plunger actuation device 70 and control circuit 78. A power source, such as replaceable or rechargeable batteries or an alternating current (A.C.) plug may be used to provide power to plunger actuation device 70 and circuit 78.

Figure 5:
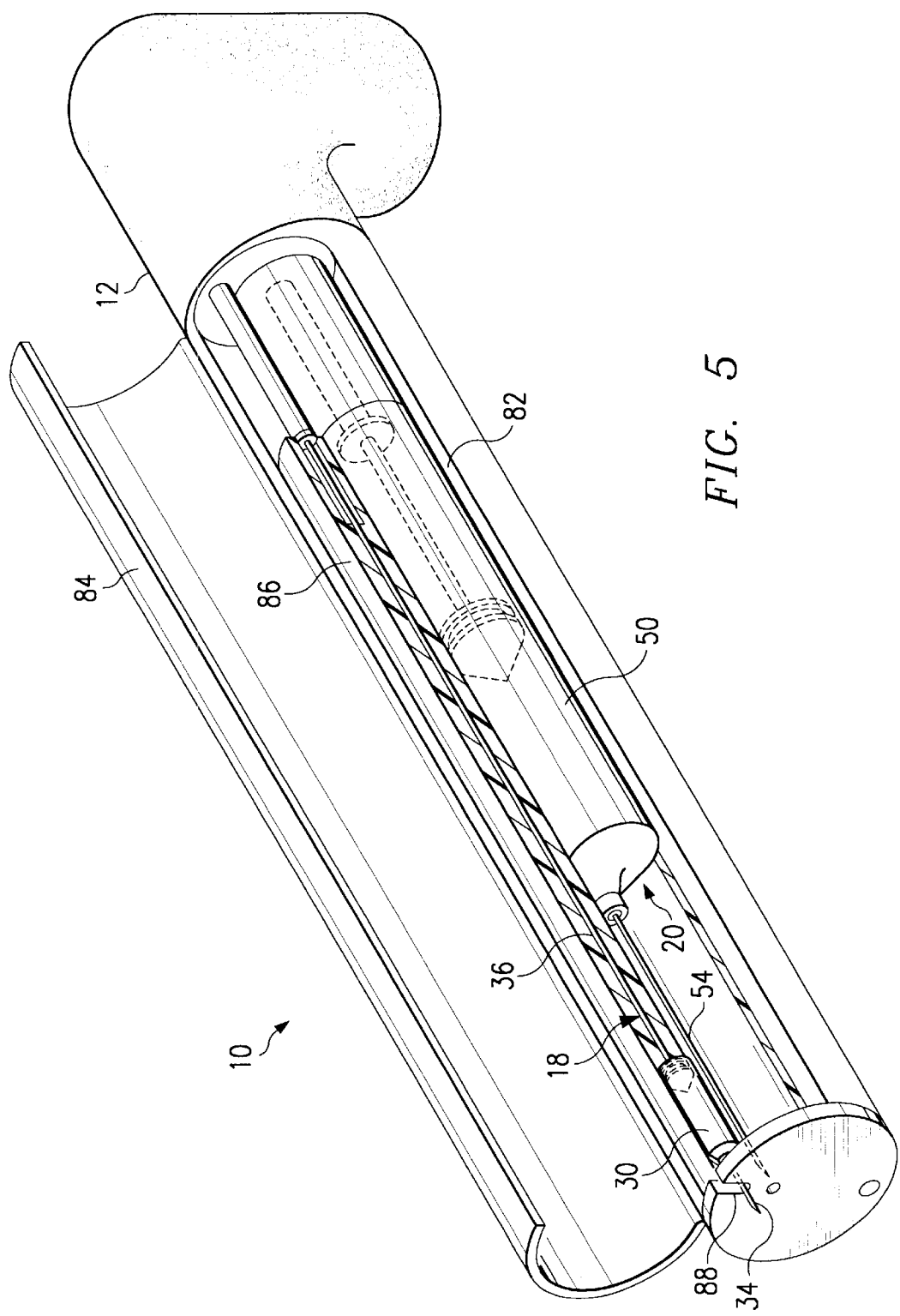
FIG. 5 is a side view of an embodiment of the injection device using a disposable cartridge containing both a medication storage chamber coupled to a first needle and a numbing agent storage chamber coupled to a second fine gauge needle.

Referring to FIG. 5, an external side view of an embodiment of injection device 10 is shown. Injector housing 12 may include an opening 82 with a latchable lid 84. Injectors 18 and 20, along with their respective needles 34 and 54, plungers 38 and 58, and elongated plunger members 36 and 56, may be part of a disposable cartridge 86 that can be easily inserted through opening 82 and installed in injection device 10. Note that a slot 88 may be formed at the tip of injection device 10 to easily allow needle 34 to pass through during installation of disposable cartridge 86. The tip of injection device 10 may have two openings to allow the passage of needles 34 and 54, or a single larger opening may be used. It is preferable that the exterior form of injection device 10 not resemble a gun, a syringe, or any device known to inflict pain to further lessen the patient's anxiety.

Referring to FIG. 6, an alternate embodiment of an injection device 100 constructed according to the teachings of the present invention is shown. Injection device 100 includes an injector housing 102 which contains a first and second inner housing portions 104 and 106. Housing portion 104 accommodates a first injector 108 and housing portion 106 accommodates a second injector 110. First injector 108 includes a storage chamber 112 containing a numbing agent 114, a fine gauge needle 116, a plunger 120, and an elongated plunger member 118. First injector 108 may also accommodate a disposable cartridge having two chamber sections that contain a numbing agent and a sodium bicarbonate solution. Second injector 110 includes a storage chamber 130 containing a numbing agent 132, a needle 134, a plunger 140, and an elongated plunger member 136. Storage chamber 130 and needle 134 of second injector 110 may form a disposable unit that includes a threaded coupling 138 for securely fastening to elongated plunger member 136 of injection device 100. This embodiment is equally applicable to first injector 108, so that its storage chamber 112 and needle 116 also form a disposable and detachable unit. Such disposable units having medication supplied in a storage chamber with an injection needle is commercially available and can be readily adapted to injection device 100 of the present invention.

In order to utilize commercially available disposable medication cartridges, injection device 100 employs an alignment of injectors 108 and 110 at a predetermined acute angle, α. The length of needles 116 and 124 and the angle α may be selected such that when fully extended, needles 116 and 134 do not interfere with one another and that needle 134 enters the patient's skin at close proximity to the entry site of numbing needle 116. The intent is that pain and discomfort caused by the insertion of needle 134 is greatly reduced or eliminated by the skin wheal created by numbing agent 114 injected by numbing needle 116. The angle, α, between needles 116 and 134 may be created by slightly angling injector 110 with respect the longitudinal axis of injection device 100, as shown in FIG. 6, or angling injector 108 or both injectors 108 and 110 to arrive at the desired injector arrangement for the particular application.

Referring to FIG. 7, yet another embodiment of an injection device 160 constructed according to the teachings of the present invention is shown. Injection device 160 includes a disposable cartridge 162 and a plunger unit 164. Disposable cartridge 162 contains a first injector 170 and a second injector 172. First injector 170 includes a storage chamber 174 containing a numbing agent 176, a fine gauge numbing needle 177, a plunger 180, and an elongated plunger member 178. A two-chamber disposable cartridge containing a numbing agent and a sodium bicarbonate solution may also be used. Second injector 172 includes a storage chamber 190 containing a pre-formulated medication 194, a needle 196, a plunger 198, and an elongated plunger member 224. Second injector 172 is accommodated in an elongated chamber, slot or guides 192 that defines an advancement path therefor. It may be seen that first and second injectors 170 and 172 are not arranged in parallel with one another but at an acute angle, α. As described above, the angular alignment puts the entry site of both needles 177 and 196 in close proximity with one another as to optimize the anesthetizing effect of numbing agent 176.

When a lidocaine and sodium bicarbonate solution is used as a numbing agent, storage chamber 30 is preferably equipped with two separate chamber sections that allow lidocaine (or other local anesthetic) and sodium bicarbonate to be stored separately. When plunger 180 is actuated, lidocaine and sodium carbonate are forced out of the separate chamber sections and mix in needle 177, and the mixture is injected into the patient's skin. The separate chamber section embodiment of the present invention may be used for storing other solution components that are not stable when mixed.

A threaded coupling 200 is further provided to securely fasten plunger 198 to elongated plunger member 224. Storage chamber 174 and needle 177 of first injector 170 and storage chamber 190 and needle 196 of second injector 172 form a disposable cartridge or unit 162. A cap 210 that may be snapped off or removed from disposable cartridge 162 may be provided to protect protruding needle 177 from undesirable contact with unsterile surfaces which may contaminate or bend needle 177.

Plunger unit 164 may include a screw-locking ring 202 which further receives storage chamber 190 and fastens thereto. Plunger unit 164 may also include finger rings 220 and 222 disposed opposingly with one another, and a thumb ring 226 coupled to the end of elongated plunger member 224.

In operation, plunger unit 164 is coupled or screwed onto disposable cartridge 162 by threaded coupling 200 and screw-locking ring 202. The user may hold injection device 160 with his/her index finger in finger ring 220 and middle finger in finger ring 222, and thumb inserted in thumb ring 226. Cap 210 may then be snapped off or removed, and injection device 160 is held substantially perpendicularly against the patient to insert needle 177 into the patient's skin. With the user's free hand, plunger 180 is pushed to inject numbing agent 176 into the patient's skin through needle 177. While holding disposable cartridge 162 with his/her free hand, plunger unit 164 is pushed against storage second injector 172 to advance it along advancement path 192 and cause needle 196 to penetrate the patient's skin and underlying tissues. The depth of needle penetration can be controlled by the user by how far he/she advances the needle, or by the length of needle 196, which may be selected for the desired depth of injection and to optimize the effect of the medication being injected. The user then pulls back plunger 198 slightly with thumb ring 226 (with finger rings 220 and 222 remaining stationary) to aspirate for the presence of blood. With a transparent cartridge housing, the presence of blood is visually detectable. In the absence of blood, the user's thumb then pushes thumb ring 226 toward injector 172 with finger rings 220 and 222 remaining stationary. The advancement of plunger 198 then evacuates storage chamber 190 and injects medication 194 intramuscularly or subcutaneously through needle 196. The needle may then be retracted into the disposable cartridge to prevent the health care worker being accidentally stuck by the contaminated needle.

It is contemplated by the present invention that plunger actuation device 70 and control circuit 78 (FIG. 1) may be interchangeably implemented as the manual plunger unit 164 (FIG. 7), and vice versa. The use of plunger actuation device 70 and control circuit 78 advantageously provides automatic actuation, needle penetration amount, aspiration for blood, and the withdrawal of the needles into the housing. It is contemplated that injection devices 100 and 160 may be equipped with plunger actuation device 70 and control circuit 78 to provide automatic actuation.

Referring to FIG. 9, a cross-sectional diagram of exemplary mechanical coupling and actuation mechanism of the plungers is shown. Injection device 300 includes a disposable portion 302 that snaps and securely couples with a handle portion 304. As shown, handle portion 304 may include a flange 303 around its tip that engages a groove defined in disposable portion 302. Disposable portion 302 includes a first and a second disposable injectors 310 and 312. As described above, injector 310 may be used to inject a small amount of anesthetic agent or saline solution into the upper skin layers to numb the injection site, and injector 312 is then used to painlessly inject a medication subcutaneously or intramuscularly.

The ends 314 and 316 of first and second injectors 310 and 312, respectively, include generally inwardly radially configured finger projections 315 and 317 which point generally toward the longitudinal centers of injectors 310 and 312. The tips of finger projections 315 define a first generally circular opening, and the tips of finger projections 317 define a second generally circular opening, as shown in FIG. 10. Finger projections 315 and 317 are constructed of plastic materials, for example, which may be sufficiently rigid but somewhat flexible. In particular, the finger projections may be integrally constructed with the chamber housing, as in finger projections 315 of injector 310 or be of a separate construction, as in finger projections 317 of injector 312. Injector 312 includes a cup-shaped receptacle 355 which is coupled to elongated member or extension rod 354 and plunger 353. Formed in the inside surface of injector storage chamber 312 is a circumferential rib 356 that protrudes slightly inwardly. The operations of injector 312 enabled by these structures are described in detail below by referring to FIGS. 11A–11P.

Injectors 310 and 312 further include injector needles 361 and 363, which are adapted to advance and protrude beyond the end of injection device 300 and enter the patient's skin to reach a certain predetermined depth. The thickness of stops 360 and 362 combined with the total length of the needles are used to determine the depth of needle penetration.

Injectors 310 and 312 also include plungers 350 and 353. Plunger 350 of injector 310 includes an extension rod 351 and a distal end portion 352. Similarly, plunger 353 of injector 312 includes an extension rod 354 and a distal end portion 355. Distal end portions 352 and 353 each may include a generally concave depression or receptacle, which is adapted to receive an enlarged and generally spherical end 330 and 332 of actuation rods 320 and 322. Enlarged spherical ends 330 and 332 are respectively larger than the openings defined by finger projections 315 and 317, respectively. Actuation rods 320 and 322 are in meshed engagement with and actuated by a cog gear 323 and 325 which are coupled to center rods 324 and 326, respectively, which are adapted to receive actuation signals from plunger actuation devices 70. The trans-axial rotation of cog gears 324 and 326 is adapted to cause actuation rods 320 and 322, respectively, to advance toward or retreat from injectors 310 and 312.

A sensor 370 may be positioned proximate to the ends 314 and 316 of injectors 310 and 312 to detect the proper advancement and retreat of actuation rods 320 and 322. Light source 76 and sensor 77 may be positioned near the ends of injectors 310 and 312 to detect aspirated blood. Sensors 76 and 370 are capable of producing electrical signals which are received by control circuit 78 and used to control plunger actuation device 70.

Figures 11A, 11B:
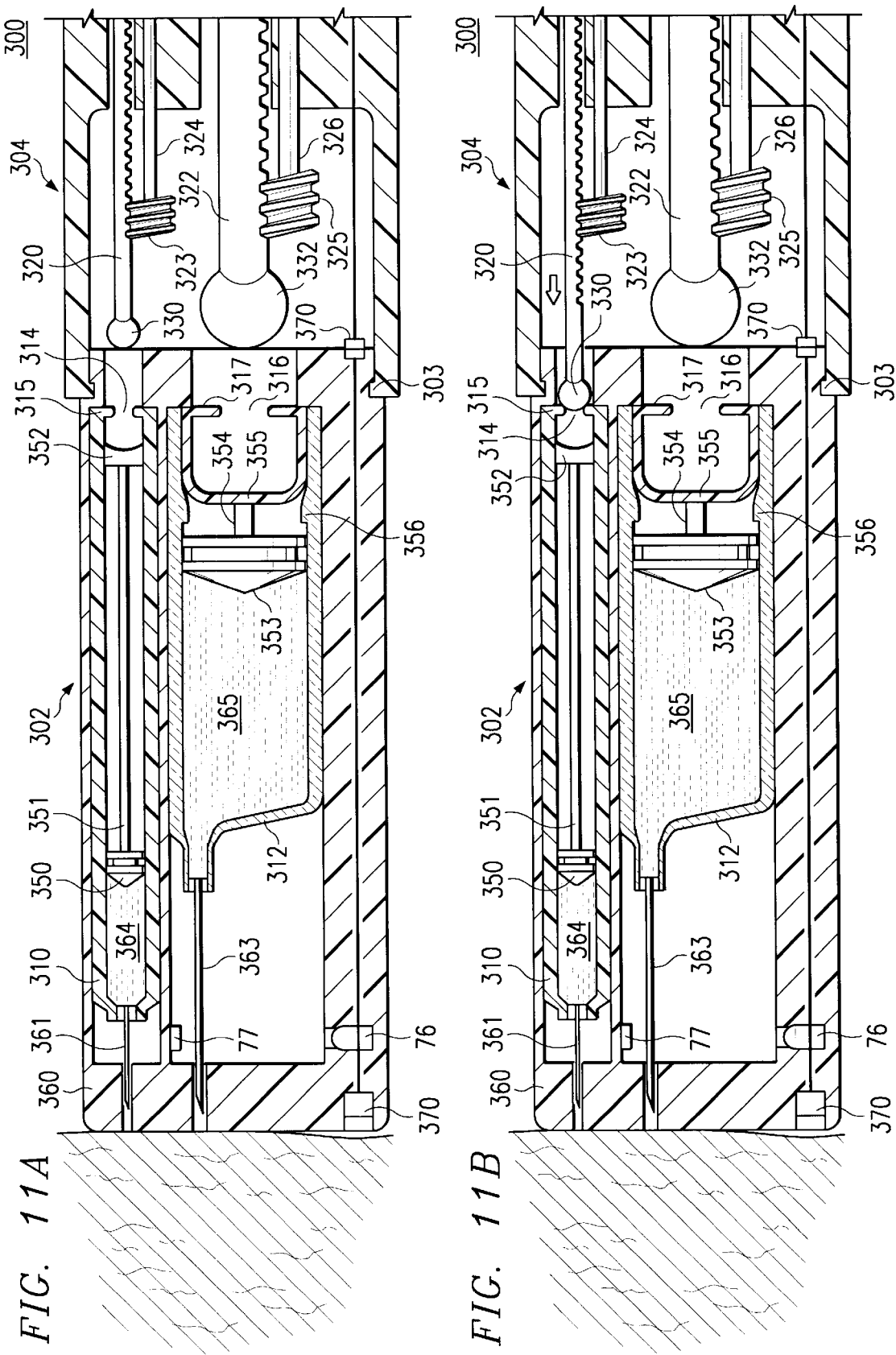
FIGS. 11A–11P are sequential cross-sectional views demonstrating the operation of the exemplary mechanical coupling and actuation mechanism of the injection device according to the teachings of the present invention.

FIGS. 11A–11P demonstrate the preferred operational sequence of injection device 10. For the purpose of simplicity and clarity, only the operation of primary injector 312 is shown in FIGS. 11A–11P. However, the operational sequence shown is generally applicable to numbing injector 310. Any difference is set forth below.

In FIG. 11A, both injectors 310 and 312 and their respective plungers 350 and 353 are at a first or neutral position, where needles 361 and 363 are completely within the disposable housing of injection device 300 and the numbing agent and medicated solution are fully contained within the storage chambers. As set forth above, first injector 310 with numbing needle 361 may also be installed into injection device 300 with the needle exposed and ready for use.

FIGS. 11B–11G are sequential cross-sectional views demonstrating the operation of numbing injector 310. As set forth above, injector 310 is operable to painlessly inject a numbing agent into the upper layers of the patient's skin in order to numb and prepare the injection site for the subcutaneous or intramuscular injection. The health care professional may initiate or begin the injection procedure by pressing a button or a switch (not shown) located on the injector housing and holds the end of the injection device to the patient's skin against the intended injection site.

In response to a start signal generated by the pressed button or switch, actuation device 70 is actuated to rotate center rod 324 and cog gear 323 which in turn advances actuation rod 320 toward distal end 314 of injector 310, as shown in FIG. 11B. The general direction of displacement is indicated by the arrow shown in each cross-sectional view. The actuation may be initiated by an actuation signal issued by control circuit 78 in response to the start signal. Because finger projections 315 are somewhat rigid and the enlarged spherical end 330 of actuation rod 320 is larger than the opening defined by finger projections 315, injector 310 is advanced by the advancing actuation rod so that its needle 361 protrudes beyond the end of injection device housing and penetrates the patient's skin, as shown in FIG. 11C. The needle advances up to a predetermined depth as determined by the length of the needle and the amount of displacement actuated by actuation rod 320. When the end of injector 310 at the base of the needle butts up against stop 360 located at the end of the injection device housing, the continued advancement of actuation rod 320 causes enlarged spherical end 330 to push through the substantially circular opening 314 formed by finger projections 315 and comes to rest against distal end portion 352, as shown in FIG. 11D. The continued displacement causes plunger 350 to push against the numbing agent stored in injector 310 storage chamber and forcing it to pass out through needle 361 and become injected into the patient's skin. This is shown in FIG. 11E.

Figure 11G:
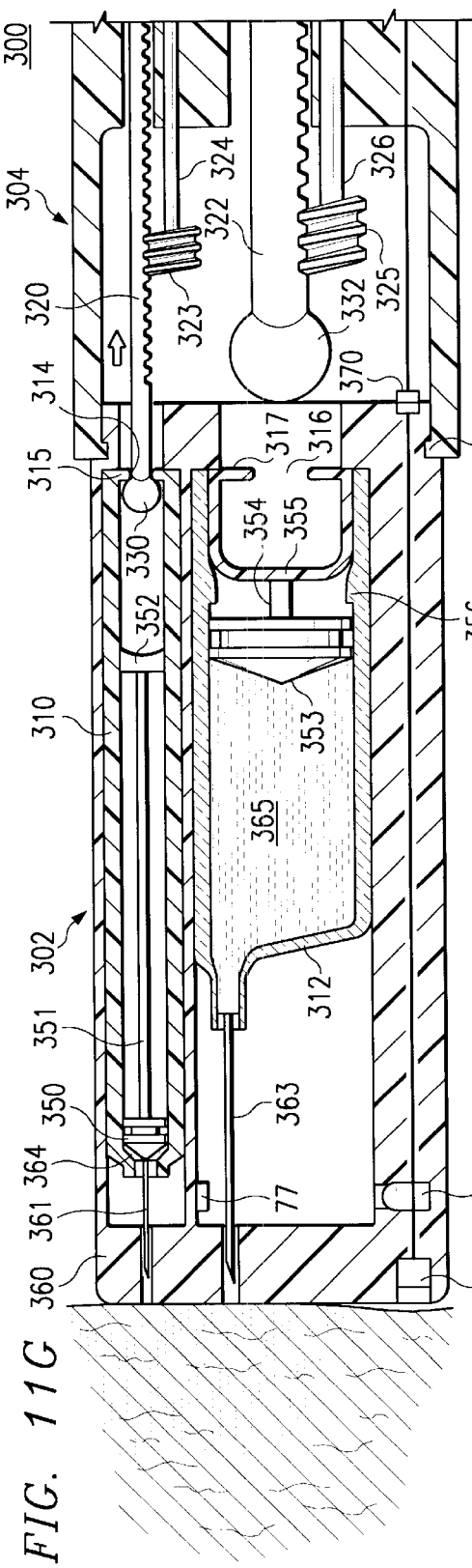
Figure 11H:
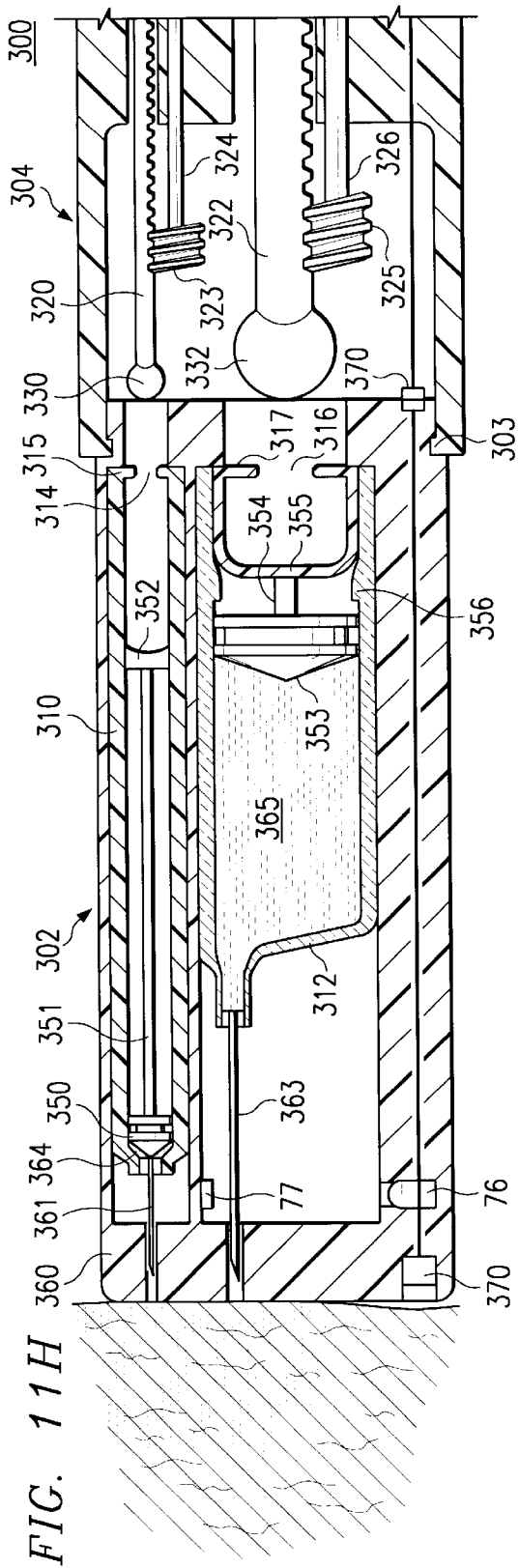

When the amount of actuation rod displacement indicates that the storage chamber is substantially fully evacuated of the numbing agent or some other indication, actuation device 70 generates a signal to retract injector 310 and its needle from the patient's skin. The withdrawing actuation rod 320 is first pulled against finger projections 315, as shown in FIG. 11F, which causes first injector 310 to retract and its needle 361 to be withdrawn from the patient's skin, as shown in FIGS. 11F and 11G. In FIG. 11H, the injection device is returned to its neutral position, but poised for the injection of the medicated solution in the second injector.

Figure 11I:
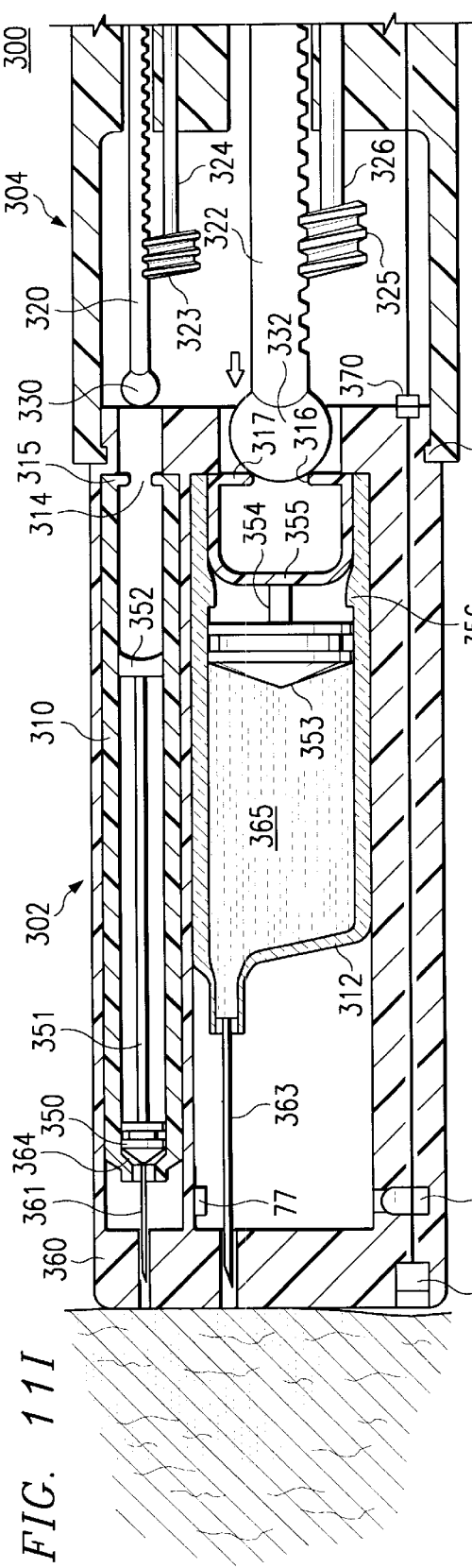
Figure 11J:
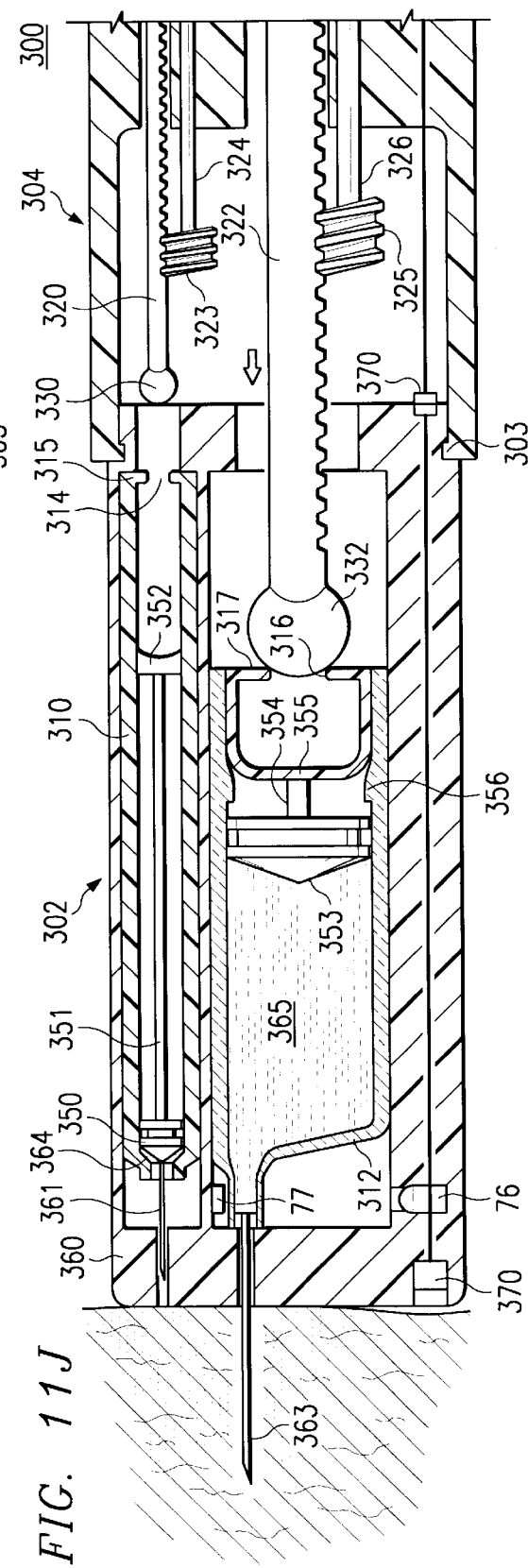

After the skin is numbed by the injection of numbing agent by injector 310, injection device 300 prepares for the primary injection of the medicated solution. In FIG. 11I, actuation device 70 is actuated to rotate center rod 326 and cog gear 325 which in turn advances actuation rod 322 and its enlarged spherical end 332 toward opening 316. In FIG. 11I, enlarged spherical end 332 is pressed against finger projections 317. The continued advancement of actuation rod 322 and enlarged spherical end 332 causes enlarged spherical end 332 to push against finger projections 317 which causes second injector to advance to the end of the injection device housing. In this manner, needle 363 is inserted into the patient's tissues reaching a desired depth, as shown in FIG. 11J. In FIG. 11K, the continued advancement of actuation rod 322 causes enlarged spherical end 332 to enter through narrow opening 316 past finger projections 317. Enlarged spherical end 332 is now seated in cup-shaped receptacle 355 and cup-shaped receptacle 355 is pushed against circumferential rib 356. It may be seen that the tip of injector 312 comes to rest against the end of injector housing, which may be used to conveniently determine the desired injection depth for needle 363. It may be seen that when cup-shaped receptacle 355 rests against circumferential rib 356, the length of extension rod 354 between plunger 353 and receptacle 355 creates a distance between plunger 353 and circumferential rib 356. This is the aspiration displacement distance.

Thereafter as shown in FIG. 11L, actuation device 70 generates a signal to cause actuation rod 322 to be pulled back the aspiration displacement distance defined between plunger 353 and circumferential rib 356 in order to aspirate for blood. This action causes plunger 353 to be pulled back a distance sufficient to draw fluids into the storage chamber to determine whether the tip of needle 363 has stopped intravascularly. If blood is detected by sensor 77, then the tip of needle 363 is intravascular, and the needle has to be repositioned in order to properly inject the medication intramuscularly or subcutaneously. Recall that the absence of light emitted by LED 76 and detected by sensor 77 indicates that needle 363 has stopped intravascularly and blood has been aspirated into the medicine chamber.

If no blood is aspirated into the medication chamber, then the needle is positioned correctly. Actuation device 70 is instructed by an inject signal from control circuit 78 to advance plunger 353 to substantially evacuate the medicated solution from the chamber which is injected into the patient's skin or muscle tissues, as shown in FIG. 11M. Actuation rod 322 is shown in FIG. 11M in its fully extended position.

At the issuance of a withdraw actuation signal, actuation rod 322 is pulled back from concave depression 355 of plunger 353 by the counter-rotation of cog gear 326. As shown in FIG. 11N, actuation rod 322 withdraws enlarged spherical end 332 and cup-shaped receptacle 355 until it rests against circumferential rib 356. Continued withdrawing of actuation rod 322 causes receptacle 355 to pull back on circumferential rib 356 which further causes injector 312 to be withdrawn from the end of the injector housing and its needle 363 to be withdrawn from the patient's skin and completely into the injector housing, as shown in FIG. 11O. At this point, second injector 312 comes to rest against a stop formed in the injector housing, which halts its further retreat.

In FIG. 11P, the continued withdrawal of actuation rod 322 causes enlarged spherical end 332 to back out past radial finger projections 317 and to be completely retreat back into handle portion 304 of injection device 300. Sensor 370 detects the complete retreat of actuation rods 320 and 322 and spherical ends 330 and 332 into the handle portion, and signals to control circuit 78 process completion.

In this position, disposable portion 302 including spent medication cartridges and needles may be completely detached from handle portion 304 of injection device 300 and be properly discarded or disposed of according to health regulations.

It may be seen from the foregoing that the various embodiments of the present invention provide an essentially painless and automatic intramuscular or subcutaneous injection with the convenience of one integrated injection device. Additionally, with the use of pre-filled medication cartridges, the incidence of dosage errors is greatly reduced. Also "wrong medication errors" are reduced because the prefilled medication label is visible through the transparent disposable cartridge. With automatic aspiration, the occurrence of injecting a medication intravascularly when an intramuscular or subcutaneous injection is intended is eliminated. Further, the injection device lessens the patient's anxiety and resulting muscle tightening at the sight of a large needle, because only a small fine gauge needle may be visible.

Although the present invention has been described in detail, it should be understood that various changes, mutations, substitutions and alterations can be made thereto without departing from the spirit and scope of the present invention as defined by the appended claims.

What is claimed is:

1. A painless injection apparatus, comprising:
    a first injector having a needle, a plunger, and a storage chamber storing a numbing agent;
    a second injector having a needle, a plunger, and a storage chamber storing a medication;
    a housing accommodating the first and second injectors;
    a plunger actuation device coupled to both the first and second injectors, the plunger actuation device operable to sequentially actuate the plungers of the first and second injectors to first inject the numbing agent at a first predetermined depth and to second inject the medication at a second predetermination depth into a patient's tissues, and wherein the plunger actuation device includes a mechanism for retracting the needles of the first and second injectors within the housing, the plungers of the first and second injectors being actuated by a single actuation of the plunger actuation device.

2. The painless injection apparatus, as set forth in claim 1, wherein the needles of the first and second injectors are positioned in close proximity with one another, so that when actuated by the plunger actuation device, the needles penetrate the patient's tissues at substantially the same site.

3. The painless injection apparatus, as set forth in claim 1, wherein the first and second injectors are aligned at an acute angle with one another, so that when actuated by the plunger actuation device, the needles penetrate the patient's tissues at substantially the same site.

4. The painless injection apparatus, as set forth in claim 1, wherein the needle of the first injector is a fine gauge needle.

5. The painless injection apparatus, as set forth in claim 1, wherein the first injector further comprises an elongated plunger member coupled to the plunger of the first injector adapted to advance the plunger in response to an actuation signal generated by the plunger actuation device.

6. The painless injection apparatus, as set forth in claim 1, wherein the second injector further comprises an elongated plunger member coupled to the plunger of the second injector adapted to advance the plunger in response to an actuation signal generated by the plunger actuation device.

7. The painless injection apparatus, as set forth in claim 1, wherein the plunger actuation device comprises a plunger unit having two finger rings and a thumb ring.

8. The painless injection apparatus, as set forth in claim 1, wherein the first injector is a disposable unit.

9. The painless injection apparatus, as set forth in claim 1, wherein the second injector is a disposable unit.

10. The painless injection apparatus, as set forth in claim 1, wherein the first and second injectors form a disposable unit.

11. The painless injection apparatus, as set forth in claim 1, further comprising a cap shielding the needle of the first injector.

12. The painless injection apparatus, as set forth in claim 1, further comprising a cap shielding the needles of the first and second injectors.

13. The painless injection apparatus, as set forth in claim 1, further comprising a mechanical coupling adapted to securely fasten the plunger of the first injector to the plunger actuation device.

14. The painless injection apparatus, as set forth in claim 1, further comprising a mechanical coupling adapted to securely fasten the plunger of the second injector to the plunger actuation device.

15. The painless injection apparatus, as set forth in claim 1, wherein the storage chamber of the first injector comprises two chamber sections operable to separately store the numbing agent and a solution.

16. The painless injection apparatus, as set forth in claim 1, further comprising a mechanism for advancing and retracting the first and second injectors and the plungers thereof in a predetermined sequential manner.

17. The painless injection apparatus, as set forth in claim 1, wherein the storage chamber of the first injector comprises two chamber sections having a common path to the needle of the first injector.

18. The painless injection apparatus, as set forth in claim 1, wherein the mechanism comprises a cog gear arrangement.

19. A painless injection apparatus comprising:
a first injector having a needle, a plunger, and a storage chamber storing a numbing agent;
a second injector having a needle, a plunger, and a storage chamber storing a medication;
a housing accommodating the first and second injectors;
a plunger actuation device coupled to both the first and second injectors, the plunger actuation device operable to sequentially actuate the plungers of the first and second injectors to first inject the numbing agent at a first predetermined depth and to second inject the medication at a second predetermination depth into a patient's tissues, and wherein the plunger actuation device includes a mechanism for retracting the needles of the first and second injectors within the housing;
a light source operable to emit a light through the storage chamber of the second injector and the medication contained therein;
a light detector operable to detect the light and generate a detection signal indicative of whether the light is detected; and
a control circuit operable to receiving the detection signal and generating an actuation signal operable to advance the plunger of the second injector in response to the light detector detecting the light.

20. A painless injection apparatus, comprising:
a first injector having a needle, a plunger, and a storage chamber storing a numbing agent;
a second injector having a needle, a plunger, and a storage chamber storing a medication;
a housing accommodating the first and second injectors;
a plunger actuation device coupled to both the first and second injectors, the plunger actuation device operable to sequentially actuate the plungers of the first and second injectors to first inject the numbing agent at a first predetermined depth and to second inject the medication at a second predetermination depth into a patient's tissues, and wherein the plunger actuation device includes a mechanism for advancing and retracting the needles of the first and second injectors within the housing in a predetermined sequential manner, wherein the mechanism, wherein the mechanism comprises:
a plurality of finger projections coupled to the storage chamber of the first injector, the plurality of finger projections defining an opening through which the plunger of the first injector is accessible;
an actuation rod coupled to the plunger actuation device, the actuation rod having an enlarged end larger than the opening defined by the plurality of finger projections; and
whereby the plunger actuation device is operable to advance the actuation rod toward the storage chamber of the first injector and causing the actuation rod to push against the plurality of finger projections and thus advancing the storage chamber and needle of the first injector to an injection position, the continued advancement of the actuation rod causing the enlarged end of the actuation rod to be forced past the plurality of finger projections through the opening defined thereby, whereby the plunger actuation device is further operable to retract the actuation rod away from the storage chamber of the first injector and causing the actuation rod to be pulled against the plurality of finger projections and thus retracting the storage chamber and the needle of the first injector to a retracted position, the continued retraction of the actuation rod causing the enlarged end of the actuation rod to be forcibly extracted past the plurality of finger projections.

21. The painless injection apparatus, as set forth in claim 20, wherein the opening defined by the plurality of finger projections is substantially circular, and the enlarged end of the actuation rod is substantially spherical.

22. A painless injection apparatus, comprising:

a first injector having a needle, a plunger, and a storage chamber storing a numbing agent;

a second injector having a needle, a plunger, and a storage chamber storing a medication;

a housing accommodating the first and second injectors;

a plunger actuation device coupled to both the first and second injectors, the plunger actuation device operable to sequentially actuate the plungers of the first and second injectors to first inject the numbing agent at a first predetermined depth and to second inject the medication at a second predetermination depth into a patient's tissues, and wherein the plunger actuation device includes a mechanism for retracting the needles of the first and second injectors with in the housing;

a mechanism for advancing and retracting the first and second injectors and the plungers thereof in a predetermined sequential manner, wherein the mechanism comprises:

a plurality of finger projections coupled to the storage chamber of the second injector, the plurality of finger projections defining an opening through which the plunger of the second injector is accessible; and an actuation rod coupled to the plunger actuation device, the actuation rod having an enlarged end larger than the opening defined by the plurality of finger projections; and whereby the plunger actuation device is operable to advance the actuation rod toward the storage chamber of the second injector and causing the actuation rod to push against the plurality of finger projections and thus advancing the storage chamber and the needle of the second injector to an injection position, the continued advancement of the actuation rod causing the enlarged end of the actuation rod to be forced past the plurality of finger projections through the opening defined thereby, whereby the plunger actuation device is further operable to retract the actuation rod away from the storage chamber of the second injector and causing the actuation rod to be pulled against the plurality of finger projections and thus retracting the storage chamber and the needle of the second injector to a retracted position, the continued retraction of the actuation rod causing the enlarged end of the actuation rod to be forcibly extracted past the plurality of finger projections.

23. The painless injection apparatus, as set forth in claim 22, wherein the opening defined by the plurality of finger projections is substantially circular, and the enlarged end of the actuation rod is substantially spherical.

24. The painless injection apparatus, as set forth in claim 22, further comprising:

a cup-shaped receptacle coupling the plurality of finger projections to the plunger of the second injector, the cup-shaped receptacle receiving the enlarged end of the second actuation rod;

a circumferential rib defined inside the first injector;

whereby the circumferential rib is operable to stop the cup-shaped receptacle and therefore the plunger from further advancement into the storage chamber until the needle is in the injection position, the circumferential rib is further operable to stop the plunger from further retraction when aspirating for blood, the circumferential rib is operable to catch the cup-shaped receptacle during retraction and therefore causing the second injector and its needle to retract within the injector housing.

25. A painless injection apparatus comprising:

a first injector having a needle, a plunger, and a storage chamber storing a numbing agent;

a second injector having a needle, a plunger, and a storage chamber storing a medication;

a housing accommodating the first and second injectors;

a plunger actuation device coupled to both the first and second injectors, the plunger actuation device operable to sequentially actuate the plungers of the first and second injectors to first inject the numbing agent at a first predetermined depth and to second inject the medication at a second predetermination depth into a patient's tissues, and wherein the plunger actuation device includes a mechanism for retracting the needles of the first and second injectors within the housing;

a handle portion housing the plunger actuation device; and a disposable portion housing the first and second injectors.

26. A method for painless injections, comprising:

automatically inserting a needle of a first injector into a patient's skin to a first predetermined depth and then automatically advancing a plunger of the first injector to inject a numbing agent stored in a storage chamber of the first injector;

automatically inserting a second needle of a second injector positioned in close proximity to the needle of the first injector into the patient's tissues to a second predetermined depth;

automatically retracting a plunger of the second injector a predetermined displacement to aspirate for blood;

determining the presence of aspirated blood in a storage chamber of the second injector by automatically emitting a light adapted to pass through the storage chamber of the second injector and the medication contained therein and automatically detecting the light and generating a detection signal in response thereto; and automatically actuating the plunger of the second injector to inject a medication stored in the storage chamber of the second injector to the second predetermined depth in the patient's tissues in response to an absence of aspirated blood.

27. A method for painless injections, comprising:

automatically inserting a needle of a first injector into a patient's skin to a first predetermined depth and then automatically advancing a plunger of the first injector to inject a numbing agent stored in a storage chamber of the first injector;

automatically actuating the plunger of the first injector to retract the needle from the patient's skin;

automatically inserting a second needle of a second injector positioned in close proximity to the needle of the first injector into the patient's tissues to a second predetermined depth, retraction of the needle of the first injector being made prior to inserting the needle of the second injector;

automatically retracting a plunger of the second injector a predetermined displacement to aspirate for blood;

determining the presence of aspirated blood in a storage chamber of the second injector; and automatically actuating the plunger of the second injector to inject a medication stored in the storage chamber of the second injector to the second predetermined depth in the patient's tissues in response to an absence of aspirated blood.

28. A method for painless injections, comprising:

automatically inserting a needle of a first injector into a patient's skin to a first predetermined depth and then automatically advancing a plunger of the first injector to inject a numbing agent stored in a storage chamber of the first injector;

automatically inserting a second needle of a second injector positioned in close proximity to the needle of the first injector into the patient's tissues to a second predetermined depth, retraction of the needle of the first injector being made prior to inserting the needle of the second injector;

automatically retracting a plunger of the second injector a predetermined displacement to aspirate for blood;

determining the presence of aspirated blood in a storage chamber of the second injector;

automatically actuating the plunger of the second injector to inject a medication stored in the storage chamber of the second injector to the second predetermined depth in the patient's tissues in response to an absence of aspirated blood; and automatically actuating the plunger of the second injector to retract the needle from the patient's tissues after injecting the medication therein.

29. A method for painless injections, comprising:

automatically inserting a needle of a first injector into a patient's skin to a first predetermined depth and then automatically advancing a plunger of the first injector to inject a numbing agent stored in a storage chamber of the first injector;

automatically actuating the plunger of the first injector to retract the needle from the patient's skin and completely into an injector housing;

automatically inserting a second needle of a second injector positioned in close proximity to the needle of the first injector into the patient's tissues to a second predetermined depth, retraction of the needle of the first injector being made prior to inserting the needle of the second injector, retraction of the needle of the first injector being made prior to inserting the needle of the second injector;

automatically retracting a plunger of the second injector a predetermined displacement to aspirate for blood;

determining the presence of aspirated blood in a storage chamber of the second injector;

automatically actuating the plunger of the second injector to inject a medication stored in the storage chamber of the second injector to the second predetermined depth in the patient's tissues in response to an absence of aspirated blood; and automatically actuating the plunger of the second injector to retract the needle from the patient's tissues and completely into the injector housing after injecting the medication.

30. A method for painless injections, comprising:

generating a first actuation signal adapted to advance and insert a needle of a first injector into a patient's skin and injecting a numbing agent into the patient's skin;

generating a second actuation signal adapted to advance and insert a needle of a second injector positioned in close proximity to the needle of the first injector into the patient's skin to a desired depth, the first injector being an integral unit with the second injector;

generating a third actuation signal adapted to retract a plunger of the second injector a predetermined amount to aspirate for blood;

detecting the presence of aspirated blood; and generating a fourth actuation signal adapted to advance the plunger of the second injector and injecting a medication to the desired depth in the patient's tissues in response to not detecting the presence of aspirated blood.

31. The method, as set forth in claim 30, further comprising generating a fifth actuation signal adapted to retracting both the needles of the first and second injectors into a housing of the first and second injectors.

32. The method, as set forth in claim 30, further comprising:

automatically emitting a light adapted to pass through the second injector and the medication contained therein;

automatically detecting the light and generating a detection signal in response thereto; and automatically generating the third actuation signal adapted to inject the medication through the second needle in response to the detection signal.

33. An injection apparatus comprising:

an injector having a housing, a storage chamber storing a medication, a needle, and a plunger;

a plunger actuation device coupled to the injector, the plunger actuation device being adapted to automatically and sequentially advance the needle into a patient's tissues, withdraw the plunger to aspirate for blood, advance the plunger to inject the medication into the patient's tissues at the desired depths, and withdraw the needle into the housing;

a control circuit operable to generate an actuation signal operable to control the plunger actuation device to advance and retract the plunger; and a mechanism for advancing and retracting the needle and the plunger in a predetermined sequential manner, wherein the mechanism comprises:

a plurality of finger projections coupled to the storage chamber of the injector, the plurality of finger projections defining an opening through which the plunger of the second injector is accessible; and an actuation rod coupled to the plunger actuation device, the actuation rod having an enlarged end larger than the opening defined by the plurality of finger projections;

whereby the plunger actuation device is operable to advance the actuation rod toward the storage chamber of the injector and causing the actuation rod to push against the plurality of finger projections and thus advancing the storage chamber and the needle of the injector to an injection position, the continued advancement of the actuation rod causing the enlarged end of the actuation rod to be forced past the plurality of finger projections through the opening defined thereby, whereby the plunger actuation device is further operable to retract the actuation rod away from the storage chamber of the second injector and causing the actuation rod to be pulled against the plurality of finger projections and thus retracting the storage chamber and the needle of the injector to a retracted position, the continued retraction of the actuation rod causing the enlarged end of the actuation rod to be forcibly extracted past the plurality of finger projections.

34. The injection apparatus, as set forth in claim 33, wherein the opening defined by the plurality of finger projections is substantially circular, and the enlarged end of the actuation rod is substantially spherical.

35. The injection apparatus, as set forth in claim 33, further comprising:

a cup-shaped receptacle coupling the plurality of finger projections to the plunger of the injector, the cup-shaped receptacle receiving the enlarged end of the actuation rod;

an inner circumferential rib defined in the injector;

whereby the circumferential rib is operable to stop the cup-shaped receptacle and therefore the plunger from further advancement into the storage chamber until the needle is in the injection position, the circumferential rib is further operable to stop the plunger from further retraction when aspirating for blood, the circumferential rib is operable to catch the cup-shaped receptacle during retraction and therefore causing the injector and its needle to retract within the injector housing.

36. The injection apparatus, as set forth in claim 33, wherein the mechanism comprises a cog gear arrangement.

* * * * *

UNITED STATES PATENT AND TRADEMARK OFFICE
CERTIFICATE OF CORRECTION

PATENT NO. : 6,312,412 B1
DATED : November 6, 2001
INVENTOR(S) : V.C. Saied et al.

It is certified that error appears in the above-identified patent and that said Letters Patent is hereby corrected as shown below:

Column 1,
Line 32, insert paragraph heading,

-- SUMMARY OF THE INVENTION --

Signed and Sealed this

Twentieth Day of August, 2002

Attest:

JAMES E. ROGAN
Attesting Officer     Director of the United States Patent and Trademark Office